United States Patent [19]

Shoher et al.

[11] Patent Number: 4,698,021

[45] Date of Patent: * Oct. 6, 1987

[54] METAL FOIL FOR FORMING A DENTAL COPING AND CROWN

[76] Inventors: Itzhak Shoher, 50 Shlomo-Hamelech St., Tel-Aviv, Israel, 64386; Aharon E. Whiteman, 13 J.L. Perez St., Petach-Tikvah, Israel, 49206

[*] Notice: The portion of the term of this patent subsequent to Jun. 30, 2004 has been disclaimed.

[21] Appl. No.: 802,987

[22] Filed: Nov. 29, 1985

Related U.S. Application Data

[63] Continuation-in-part of Ser. No. 690,650, Jan. 11, 1985, abandoned.

[51] Int. Cl.$^4$ ............................................. A61C 5/08
[52] U.S. Cl. ............................. 433/222.1; 428/607; 428/669; 433/218
[58] Field of Search ............... 433/207, 208, 218, 222, 433/223, 227; 428/607, 669, 670, 672, 621, 632; 228/263.18; 3/1.9

[56] References Cited

U.S. PATENT DOCUMENTS

| | | | |
|---|---|---|---|
| 431,848 | 7/1890 | Meyer | 428/669 |
| 1,379,063 | 5/1921 | Van Allen | 428/669 |
| 2,303,497 | 12/1942 | Reeve | 428/669 |
| 3,934,348 | 1/1976 | Junjii | 433/222 |
| 3,981,723 | 9/1976 | Toccollo | 433/207 |
| 4,123,262 | 10/1978 | Cascone | 433/207 |
| 4,218,244 | 8/1980 | Knosp | 433/207 |
| 4,273,580 | 6/1981 | Shoher et al. | 433/207 |
| 4,427,501 | 1/1984 | Rogers | 3/1.9 |
| 4,434,211 | 2/1984 | Shoher et al. | 428/553 |
| 4,459,112 | 7/1984 | Shoher et al. | 433/222 |
| 4,492,579 | 1/1985 | Shoher et al. | 433/222 |

FOREIGN PATENT DOCUMENTS 180142 10/1983 Japan .................................. 433/207

*Primary Examiner*—Melvyn J. Andrews
*Assistant Examiner*—John J. Zimmerman
*Attorney, Agent, or Firm*—E. Lieberstein

[57] ABSTRACT

A metal dental coping foil for dental restoration, having a high fusing temperature layer composed of a precious metal palladium-gold alloy and at least two precious metal gold layers symmetrically disposed about the palladium-gold layer.

11 Claims, 4 Drawing Figures

METAL FOIL FOR FORMING A DENTAL COPING AND CROWN

This application is a continuation-in-part of U.S. patent application Ser. No. 690,650 filed Jan. 11, 1985, now abandoned, entitled METAL COPING AND CROWN FOR A CERAMOMETAL RESTORATION.

BACKGROUND OF INVENTION

A new technique for constructing a porcelain to metal crown having a fracture resistance comparable to or greater than the fracture resistance to impact forces of the veneer cast metal crown and which overcomes many of the shortcomings of the conventional porcelain jacket crown is disclosed in U.S. Pat. Nos. 4,273,580 and 4,459,112, respectively. In accordance with U.S. Pat. No. 4,273,580, a precious metal foil, preferably a laminate of several precious metal layers, is swaged about a prepared die of a tooth to form a metal matrix upon which a veneering material such as porcelain is fired. However, unlike the conventional porcelain jacket crown, the metal matrix is not removed or separated from the veneering material but is instead retained as a metal coping for the finished porcelain jacket crown. The metal coping is employed as an understructure in the conventional porcelain to metal cast crown.

The physical strength of the metal coping may be substantially enhanced and the ease of preparing the restoration greatly simplified by converting the metal foil starting material into a preformed coping of predetermined geometry as taught and described in U.S. Pat. No. 4,459,112 referred to above. The metal foil starting material is cut into a circular segment and folded to form multiple folds which are uniformly spaced apart and preferably extend radially from a central unfolded area. This multiple fold geometry makes it easy to adapt the preformed coping to the die without the need for superior skill and craftsmanship and even more importantly increases the strength of the coping. Although the preformed coping as above described has certain advantages, it is not essential to the practice of the present invention. In fact, any preformed shape or method of construction may be used.

A metal coping should function to both protect the tooth abutment and as a structural support for the crown or bridge. In the latter respect, the coping supports the veneer material and provides structural strength and rigidity to the dental restoration. An ideal coping will act as an extension of the vital abutment tooth to protect the tooth against fracture and to resist distortion and displacement from the forces applied when chewing food.

The strength of the metal coping after it is swaged and removed from the die is dependent upon its hardness and rigidity. These characteristics may be satisfied using a precious metal which is known to be hard and relatively rigid such as platinum. Rigidity is basically controlled by thickness. Conversely, the ability to adapt and swage the preformed coping to the die so as to assure a proper adaptation with accurate marginal fit requires the coping to be highly workable, i.e., it should be soft and flexible. To be flexible the material should be thin. A dental coping should accordingly be of a material composition which is soft and flexible when it is adapted to the die and yet is hard and rigid after adaptation so as to provide the required structural support for the restoration. These apparent contradictory requirements are met by the coping and crown construction of the present invention. The hardness or softness of a metal is determined by measuring its resistance to permanent indentation. A hardness number is assigned to the material using any one of several conventional hardness tests such as the Vickers hardness test, which uses a diamond pyramid indenter.

In the parent application, U.S. Ser. No. 690,650, the metal coping comprises a low fusing temperature component represented by a gold layer superimposed upon a high fusing temperature component represented by a layer of substantially pure palladium symmetrically disposed between equal layers substantially of gold. It was discovered that this combination of materials will function before sintering as a soft material and after sintering will convert to a harder and more rigid material. It was further discovered that the disposition of the palladium layer between equal layers substantially of gold is essential to increase the fracture resistance of the composite and to minimize any distortion from differences in thermal expansion of the metals during heat treatment.

SUMMARY OF THE INVENTION

In accordance with the present invention, it was discovered that the layer of palladium can be a palladium alloy of palladium and gold containing at least about 50% palladium and that the metal coping may alternatively be formed from a relatively thick single layer of such palladium alloy having a high fusing temperature which is symmetrically disposed between at least two layers each of equal thickness and each composed substantially or entirely of gold.

In one embodiment of the present invention, the dental coping comprises a high fusing temperature component including a single layer of a precious metal alloy containing at least about 50% palladium and two precious metal layers composed substantially or entirely of gold symmetrically disposed about the palladium layer.

In another embodiment of the present invention the dental coping comprises a high fusing temperature component including at least three layers in a laminated arrangement with one layer of a precious metal alloy containing at least about 50% palladium bounded on both sides by a substantially identical layer composed substantially or entirely of gold and a low fusing temperature component composed essentially or entirely of gold superimposed upon the high fusing temperature component.

The dental crown of the present invention comprises a metal coping including a layer of a high fusing temperature precious metal alloy containing at least about 50% palladium disposed between substantially equal precious metal layers substantially or entirely of gold and a ceramic veneer covering all or part of the metal coping.

OBJECTS AND BRIEF DESCRIPTION OF THE DRAWINGS

It is the principal object of the present invention to provide a dental crown with increased strength and resistance to fracture.

It is a further object of the present invention to provide a dental coping for a dental crown which is easily adapted to a die yet physically strong after swaging and dimensionally stable in response to heat treatment.

Other objects and advantages of the present invention will become apparent from the following detailed description of the invention when read in conjunction with the accompanying drawings of which:

DETAILED DESCRIPTION OF THE INVENTION

Figure 1:
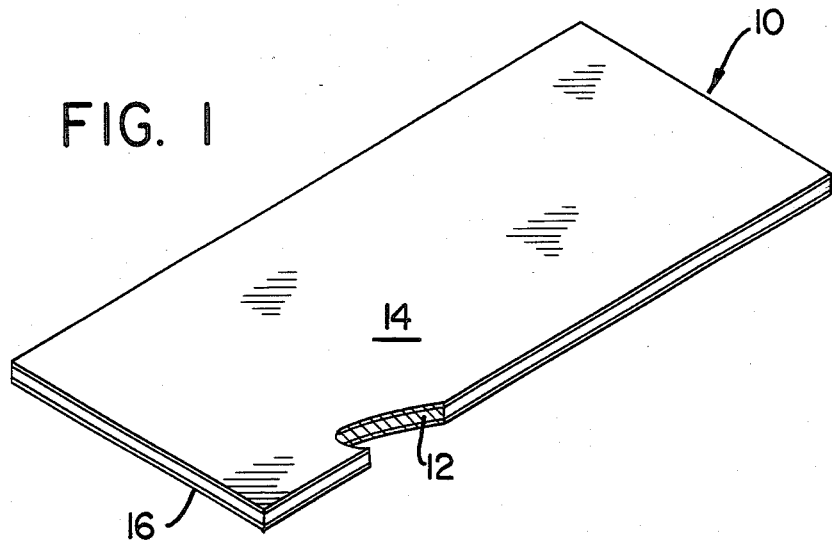
FIG. 1 is an enlarged perspective of a rectangular segment of a metal foil starting material for forming the dental coping and jacket crown of the present invention.
Figure 2:
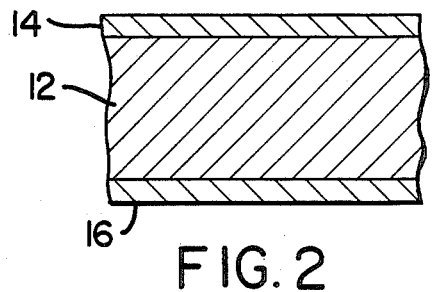
FIG. 2 is an end view of the segment of FIG. 1 showing a three layered lamination in an arrangement according to the present invention.

The metal foil starting material 10 of FIGS. 1 and 2 is a multi-layer lamination including a high fusing temperature precious metal layer 12 sandwiched between two substantially equal low fusing temperature metal layers 14 and 16 composed essentially or entirely of gold. High fusing temperature for purposes of the present invention means a melting temperature of at least about 1250° to 1300° C. whereas low fusing temperature means a melting temperature substantially equal to the melting temperature of gold. The high fusing temperature precious metal layer 12 is composed of at least about 50% palladium with the remainder preferably composed primarily of gold with one or more of the following additional elements in combination: silver, copper, iridium, platinum with the iridium element present, if at all, in small amounts relative to the other elements. The preferred composition of the high fusing layer 12 should contain about 54% palladium, 35% gold with the major portion of the remainder divided between copper and silver. A palladium and gold alloy is a relatively soft material. Upon heat treatment diffusion of palladium into the low fusing gold layers 14 and 16 occurs to cause an increase in hardness and strength in the composite coping. Heat treatment is recommended before any veneering material is applied to cause some melting of the gold layers 14 and 16 to fill voids and spaces and to form a composite coping structure. Heat treatment is also necessary to fire each layer of porcelain or other veneer composition. The location of the palladium-gold alloy layer 12 between two substantially identical gold layers 14 and 16 is still essential to the invention. This arrangement establishes dimensional stability under heat treatment and reduces the likelihood of distortion from expansion and contraction before and after porcelain baking. If layer 16 is selected to be thinner than 14 microns, then the outer layer should remain at least equal to about 14 microns to preserve a goldish background color for the porcelain.

It should be noted that in the embodiment of FIGS. 1 and 2 only a single layer of a palladium gold alloy is required for the high fusing temperature component of the present invention. Moreover, such layer of palladium and gold may be relatively thick between 25 and 50 microns with 35 microns being preferred. The gold layers may also be somewhat thicker between 8 and 30 microns and preferably about 14 microns in thickness. This increased thickness provides added body which renders the coping less fragile, easier to handle and increases its strength after adaptation.

Figure 3:
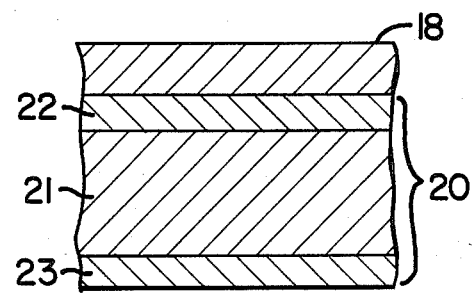
FIG. 3 is an end view of an alternate laminated arrangement for the dental coping according to the present invention.

An alternative multi-layered arrangement similar to that in the parent U.S. patent specification Ser. No. 690,650 is shown in FIG. 3 comprising a low fusing gold layer 18 superimposed over a high fusing ternary lamination 20 including a palladium-gold alloy layer 21, equivalent in composition to layer 12 of FIG. 2, bounded by gold based layers 22 and 23 respectively. The gold based layers 22 and 23 each contain from 50 to 95% gold and from 0 to 50% of one or more of the following elements in combination: silver, palladium, platinum, iridium, copper and aluminum. The principal distinction of the laminated arrangement in FIG. 3 over the arrangement in the parent application is the use of the palladium-gold alloy layer 21. Likewise, and as taught in the parent patent application, the embodiment of FIG. 3 is not limited to a high fusing component laminated arrangement with only one palladium layer bounded on each side by a gold based layer. The same arrangement can readily be expanded to include two palladium layers provided each palladium layer is bounded on each side by an equal gold based layer. Also in the embodiment of FIGS. 1 and 2 the gold layers 14 and 16 need not be single layers but each may instead represent a multiple of gold layers. For example each layer 14 and 16 can represent a combination of two or three gold based layers with the outermost layer being a low fusing temperature gold layer and another of such layers being a higher fusing temperature gold based layer such as gold layers 22 and 23 of FIG. 3. Multiple gold based layers can be used to control the dimensional stability of the composite under heat treatment and its coefficient of expansion. Regardless of the arrangement, it is necessary in the practice of the present invention to provide symmetrical layers of a gold composition on both sides of the palladium alloy composition. If multiple gold layers are used each side of the palladium layer must still be symmetrical in number of layers, thickness and composition. When the gold base component consists of high and low fusing temperature gold based layers, the high fusing layers have to be about symmetrically arranged on both sides of the palladium based layer. The low fusing temperature gold layer may be on one side or on both sides of the high fusing complex.

The high fusing complex consists of the palladium and high fusing gold base layers. A symmetrical arrangement of the low fusing gold layers over the high fusing complex is prefered.

Figure 4:
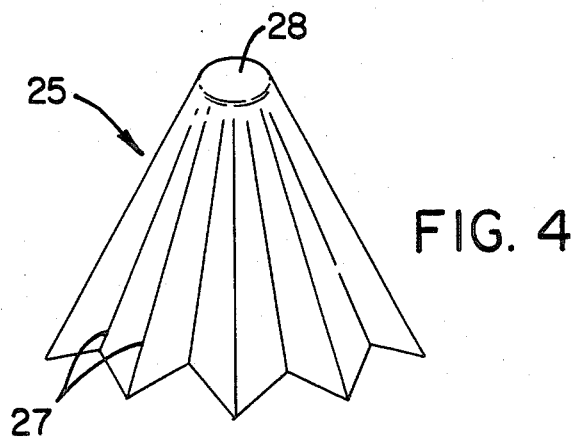
FIG. 4 is a perspective of a preferred dental coping formed from the starting material of FIG. 1 or FIG. 3.

A preformed coping 25 as shown in FIG. 4 may be formed using the laminated arrangement of FIGS. 2 or 3 or any other arrangement within the scope of the present invention. The preformed coping 25 may be formed following the procedure taught and described in U.S. Pat. No. 4,459,112. As described in the patent, the metal foil starting material 10 is cut into a blank of circular geometry and folded to form multiple fold lines 27. The fold lines 27 extend from a central unfolded area 28. Other construction techniques may likewise be used to fabricate a preformed coping and of alternate shapes. The preformed coping 25 is then placed over the die (not shown) to adapt the coping to the die using any conventional swaging device. Once the coping is adapted and removed from the die, it is heat treated by placing it over the flame of a Bunsen burner for a short time period based on flame temperature to allow the low fusing temperature gold layer 12 to flow to form a compact metal matrix without air pockets. This heat treatment may also be carried out in a furnace at a temperature of about 1020° C. to 1150° C.

After the heating step, porcelain or another veneering material can be directly applied in a conventional manner to form the dental crown of the invention. It is desirable but not essential to coat the outside surface of the metal foil before the porcelain is applied with a bonding composition to achieve an unbreakable bond between the porcelain layers and the metal coping. A preferred bonding composition is taught and described in U.S. Pat. No. 4,434,211 which includes a gold based precious metal composition in combination with a halide of a noble metal such as a gold or silver chloride. The bonding material should be sintered to the metal coping at a temperature above 1600° F. which can be achieved simultaneously with the firing of the required porcelain outer layers. The heat treatment of the porcelain is conventional and any typical firing schedule may be applied with a firing temperature generally between 1600° F. and 1820° F.

What we claim is:

1. A metal foil for use in forming a dental coping for a dental restoration comprising a high fusing temperature layer substantially composed of a precious metal palladium-gold alloy and at least two precious metal layers equally composed substantially or entirely of gold symmetrically disposed about said palladium-gold alloy layer.

2. A metal foil as defined in claim 1 wherein said precious metal palladium-gold alloy further comprises one or more elements selected from the group consisting of: silver, copper, platinum, and irridium.

3. A metal foil as defined in claim 2 wherein said palladium-gold alloy contains at least about 50% palladium.

4. A metal foil as defined in claim 3 consisting solely of a single layer of said precious metal palladium-gold alloy and a single layer of gold on each side thereof.

5. A metal foil as defined in claims 2 or 4 wherein said layer of said palladium-gold alloy has a thickness between 25 and 50 microns and wherein each layer of gold has a substantially equal thickness between about 8 to 30 microns.

6. A metal foil as defined in claim 5 wherein said layer of said palladium-gold alloy has a thickness of 35 microns and wherein each layer of gold has a thickness of 14 microns.

7. A metal foil as defined in claim 6 wherein said precious metal palladium-gold alloy comprises about 54% palladium, about 35% gold, with the remainder selected from one or more of the group of elements consisting of silver, copper, iridium and platinum.

8. A metal foil as defined in claim 1 further comprising a multi-layer arrangement having a high fusing temperature component including a palladium alloy layer and a gold based layer on each opposite side thereof and at least one low fusing temperature component of gold superimposed on said high fusing temperature component.

9. A metal foil as defined in claim 8 including at least two high fusing temperature components.

10. A dental crown comprising a metal coping including a layer of a high fusing temperature prcious metal alloy composed substantially of palladium and gold disposed between substantially equal precious metal layers substantially or entirely of gold and a ceramic veneer covering all or part of the metal coping.

11. A dental crown as claimed in claim 10 wherein said layer of said palladium and gold alloy contains at least about 50% palladium.

* * * * *